US008019420B2

(12) United States Patent
Hine et al.

(10) Patent No.: US 8,019,420 B2
(45) Date of Patent: Sep. 13, 2011

(54) MEDICAL LEAD CONNECTOR SYSTEMS WITH ADAPTERS

(75) Inventors: Douglas S. Hine, Forest Lake, MN (US); John L. Sommer, Coon Rapids, MN (US); John Gurley, Lexington, KY (US)

(73) Assignee: Medtronic, Inc., Minneapolis, MN (US)

( * ) Notice: Subject to any disclaimer, the term of this patent is extended or adjusted under 35 U.S.C. 154(b) by 326 days.

(21) Appl. No.: 10/646,545

(22) Filed: Aug. 21, 2003

(65) Prior Publication Data

US 2005/0043770 A1 Feb. 24, 2005

(51) Int. Cl.
*A61N 1/375* (2006.01)

(52) U.S. Cl. .......................................................... 607/37

(58) Field of Classification Search .................... 607/37; 439/909, 312, 322
See application file for complete search history.

(56) References Cited

U.S. PATENT DOCUMENTS

| | | | | |
|---|---|---|---|---|
| 4,142,532 | A | 3/1979 | Ware | 128/419 P |
| 4,182,345 | A | 1/1980 | Grose | 128/419 P |
| 4,469,104 | A * | 9/1984 | Peers-Trevarton | 607/37 |
| 4,583,543 | A | 4/1986 | Peers-Trevarton | 128/419 P |
| 4,628,934 | A * | 12/1986 | Pohndorf et al. | 607/27 |
| 5,000,177 | A | 3/1991 | Hoffmann et al. | 128/419 P |
| 5,007,864 | A | 4/1991 | Stutz, Jr. | 439/651 |
| 5,050,602 | A | 9/1991 | Osypka | 128/419 P |
| 5,060,649 | A | 10/1991 | Hocherl et al. | 128/419 P |
| 5,070,605 | A | 12/1991 | Daglow et al. | 29/842 |
| 5,328,442 | A | 7/1994 | Levine | 600/17 |
| 5,341,812 | A | 8/1994 | Allaire et al. | 128/696 |
| 5,423,873 | A | 6/1995 | Neubauer et al. | 607/68 |
| 5,766,042 | A | 6/1998 | Ries et al. | 439/668 |
| 5,843,141 | A * | 12/1998 | Bischoff et al. | 607/37 |
| 6,044,302 | A | 3/2000 | Persuitti et al. | 607/37 |
| 6,295,475 | B1 | 9/2001 | Morgan | 607/122 |
| 6,705,900 | B2 * | 3/2004 | Sommer et al. | 439/668 |
| 6,854,994 | B2 * | 2/2005 | Stein et al. | 439/218 |
| 6,921,295 | B2 * | 7/2005 | Sommer et al. | 439/668 |
| 2002/0115343 | A1 | 8/2002 | Sommer et al. | 439/578 |
| 2003/0050549 | A1 | 3/2003 | Sochor | 600/378 |
| 2003/0073348 | A1 | 4/2003 | Ries et al. | 439/578 |
| 2003/0077943 | A1 * | 4/2003 | Osypka | 439/623 |

* cited by examiner

*Primary Examiner* — Scott M Getzow
*Assistant Examiner* — Alyssa M Alter
(74) *Attorney, Agent, or Firm* — Carol F. Barry

(57) ABSTRACT

A lead connector including a connector element array is fitted into a selected adaptor from a plurality of adaptors to electrically couple one or more elements of the connector element array, corresponding to one or more selected electrodes from an array of lead electrodes, to one or more contact zones of the selected adaptor in order to facilitate electrical connection with an implantable medical device.

15 Claims, 10 Drawing Sheets

MEDICAL LEAD CONNECTOR SYSTEMS WITH ADAPTERS

CROSS-REFERENCE TO RELATED APPLICATION

Cross-reference is hereby made to the following commonly assigned related U.S. application Ser. No. 10/646,899 to Douglas Hine and John Sommer, filed concurrently herewith, entitled MULTI-POLAR ELECTRICAL MEDICAL LEAD CONNECTOR SYSTEM.

FIELD OF THE INVENTION

Embodiments of the present invention relate to implantable medical device connectors and more particularly to a connection system adapted to allow selection of one or more electrodes from a plurality of electrodes included on a medical electrical lead for permanent connection with the medical device.

BACKGROUND OF THE INVENTION

Implantable medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters. In the field of cardiac stimulation and monitoring, endocardial leads are placed through a transvenous route to locate one or more stimulation and/or sense electrodes, along or at the distal end of the lead body, in a desired location within a chamber of the heart or within a blood vessel of the heart. Epicardial leads are routed from a subcutaneous site to dispose one or more stimulation and/or sense electrodes, along or at the distal end of the lead body, at an epicardial site on the heart. A pacemaker implantable pulse generator (IPG) or implantable cardioverter/defibrillator (ICD) or monitor, referred to herein generically as an implantable medical device (IMD) is coupled to the heart through one or more of such endocardial or epicardial leads forming medical system. Means for implanting such cardiac leads are known to those skilled in the art of pacing and defibrillation therapy.

Proximal ends of such cardiac leads typically are formed with a lead connector assembly that is inserted into a connector bore of a connector block of the IPG or monitor. The lead body extending distally from the connector assembly typically includes one or more insulated conductors surrounded by an outer insulative sheath. Each conductor couples a lead connector contact of the lead connector assembly with a distal stimulation and/or sense electrode.

More recently, medical electrical leads have been constructed with an array of pacing and/or sensing electrodes from which one or more electrodes may be selected to optimize electrical stimulation therapy and/or monitoring. One example of such a lead is a coronary vein lead implanted to stimulate a left atrium or left ventricle; other examples include a right atrial or ventricular lead implanted to stimulate an endocardial portion of the right atrium or ventricle or leads implanted to stimulate directly a portion of the cardiac conduction system. A connection system for these types of leads needs to be adapted for the selection of one or more electrodes included in the array.

BRIEF DESCRIPTION OF THE DRAWINGS

Embodiments of the present invention will be more readily understood from the following detailed description when considered in conjunction with the drawings, in which like reference numerals indicate identical structures throughout the several views, and wherein.

The drawings are not necessarily to scale.

DETAILED DESCRIPTION OF EMBODIMENTS OF THE INVENTION

In the following detailed description, references are made to illustrative embodiments of the invention. The embodiments are described in the context of a pacing system incorporated in an implantable pacemaker or ICD comprising an ICD or pacemaker IPG (herein collectively referred to as an IMD) and at least one cardiac lead. It will be understood that more than one cardiac lead can be coupled to the IMD connector and extend to the heart in a manner well known in the art. It will be understood that the present invention can be incorporated into other medical electrical leads coupled to other IMDs through adaptors incorporating the principles of the present invention for delivering electrical stimulation elsewhere in the body. It is therefore understood that other embodiments can be utilized without departing from the scope of the invention.

The adaptors of the present invention, when assembled with a lead connector may conform to an industry standard for IMD lead connectors; however, it is not necessary to the practice of the invention that the assembly conform to an existing industry standard. Moreover, the degree to which an adaptor of the present invention "up-sizes" the lead connector can range from a negligible up-sizing to a significant up-sizing without departing from the practice of the invention.

Figure 1:
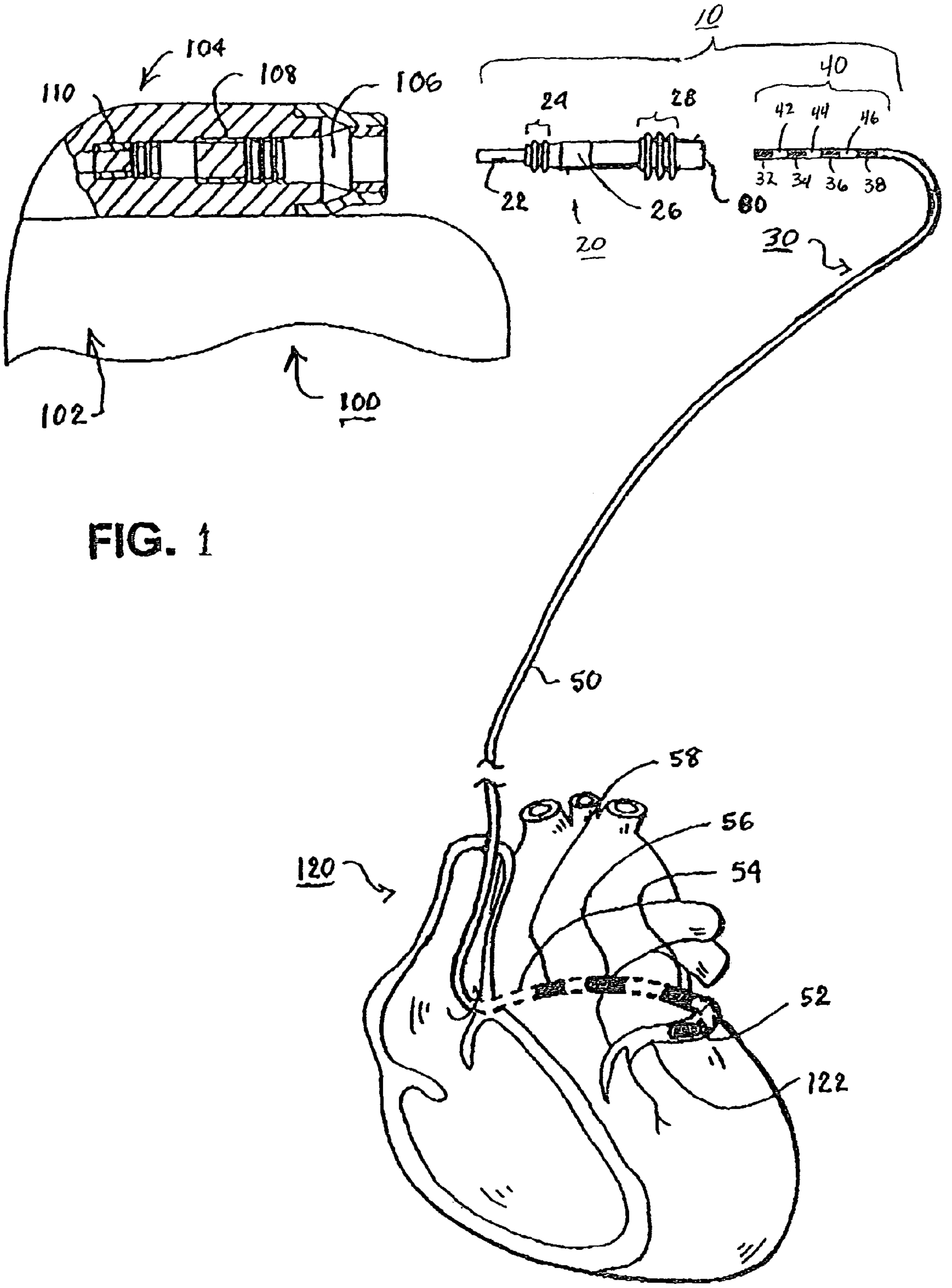
FIG. 1 is a schematic depicting an implantable medical device in part in relation to an adaptor and a connector of a cardiac lead.

FIG. 1 is a schematic depicting an IMD 100 in part in relation to an assembly 10 of an adaptor 20 and a connector 40 terminating a proximal end of a body 50 of a cardiac lead 30. As illustrated in FIG. 1, connector 40 comprises a plurality N (where N=4 in this example) of lead connector elements 32, 34, 36, 38 electrically isolated from one another and spaced apart by insulator rings 42, 44, and 46. Lead connector elements 32, 34, 36, 38 are coupled via elongated lead conductors extending through lead body 50 to a respective plurality N of distally located pace/sense electrodes 52, 54, 56, 58 spaced apart along lead body 50. According to embodiments of the present invention, one or more of a plurality of pace/sense electrodes implanted in proximity to particular pace/sense sites, such as pace/sense electrodes 52, 54, 56, 58, are selected for delivery of pacing pulses and/or sensing of the electrical signals of a heart. For example, FIG. 1 illustrates cardiac lead 30 implanted in a coronary sinus (CS) of a heart 120 wherein adaptor 20 is used to select one or more of the plurality of pace/sense electrodes 52, 54, 56, 58, which are positioned within a vein 122 branching from the CS.

As further illustrated in FIG. 1, adaptor 20 includes a lumen 80 adapted to accept insertion of connector 40, a proximal connector ring 22, a set of proximal sealing rings 24, a distal connector ring 26, and a set of distal sealing rings 28. According to embodiments of the present invention, proximal adaptor ring 22 includes an electrical contact exposed within the adaptor lumen 80 and configured to make electrical and mechanical contact with a selected one of lead connector elements 32 and 34. Similarly, distal adaptor connector ring 26 includes an electrical contact exposed within adaptor lumen 80 and configured to make electrical and mechanical contact with a selected one of lead connector elements 36 and 38. Adaptor 20 is selected from a set of adaptors 200, illustrated in FIG. 2, to correspond with a selected one or more electrodes of plurality of electrodes 52, 54, 56, and 58. According to embodiments of the present invention, the selected one or more electrodes are coupled to IMD 100 for delivery of pacing pulses and/or sensing electrical activity of heart 120 via adaptor 20.

As further illustrated in FIG. 1, IMD 100 includes a connector header 104 attached to a hermetically sealed enclosure 102 that contains a battery and electronic circuitry and other components. Connector header 104 includes a connector bore 106, adapted to receive assembly 10 of lead connector 40 inserted within adaptor 20, and two connector blocks 110 and 108 of any of the known types that are electrically connected to the electronic circuitry through feedthrough pins of feedthroughs (not shown) mounted to extend through hermetically sealed enclosure 102. Connector blocks 110 and 108 are dimensioned in diameter and are spaced apart in connector bore 106 to receive and make electrical and mechanical connection with proximal connector ring 22 and distal connector ring 26, respectively, of adaptor 20. Such electrical and mechanical connection is effected typically through the tightening of setscrews (not shown) as disclosed in U.S. Pat. Nos. 4,142,532 and 4,182,345, for example, or an action of inwardly extending force beams (not shown) as disclosed in U.S. Pat. Nos. 5,070,605 and 5,766,042, for example. When assembly 10 is inserted into connector bore 106, proximal connector ring 22 and distal connector ring 26 are seated within the axially aligned bores of the connector blocks 110 and 108, respectively, where electrical contact is made between IMD 100 and a selected pair of lead connector elements via connector rings 22 and 26. In some embodiments according to the present invention, connector blocks 110 and 108 include connection means such as setscrews, which apply force to compress connector rings 22 and 26 against the selected pair of lead connector elements in order to provide additional mechanical retention in addition to stable electrical coupling.

Figure 2:
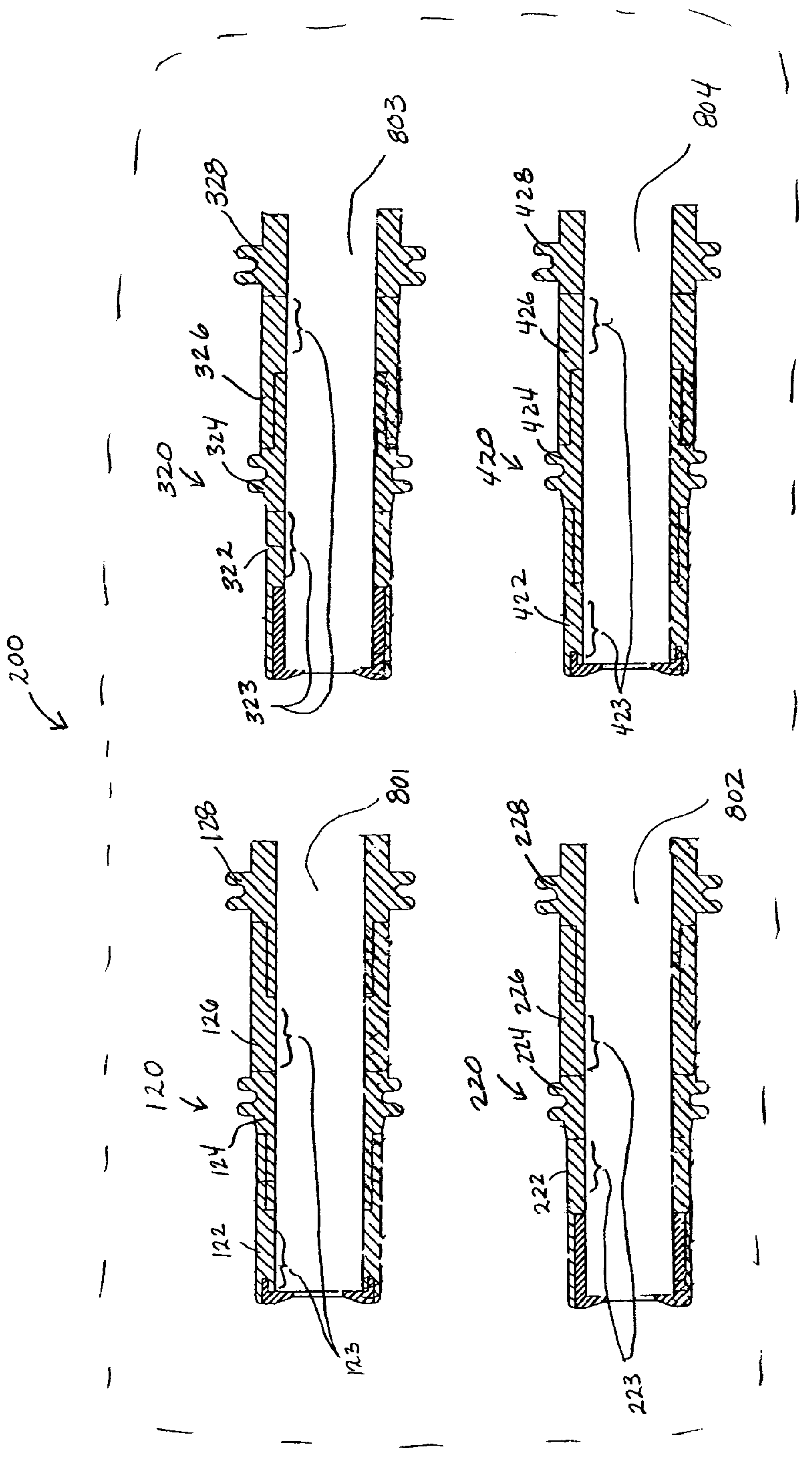
FIG. 2 is a schematic of a set of adaptors, each shown in axial cross-section, according to an embodiment of the present invention.

FIG. 2 is a schematic of a set of adaptors 200, each shown in axial cross-section, according to an embodiment of the present invention. As illustrated in FIG. 2, set 200 includes a first adaptor 120, a second adaptor 220, a third adaptor 320, and a fourth adaptor 420 including lumens 801, 802, 803, and 804, respectively. According to embodiments of the present invention each adaptor 120, 220, 320, 420 includes a pair of electrical contact zones 123, 223, 323, and 423, respectively; each pair of contact zones 123, 223, 323, and 423 associated with connector rings 122 and 126, 222 and 226, 322 and 326, and 422 and 426, respectively. As is further illustrated in FIG. 2, each adaptor 120, 220, 320, and 420 includes a set of proximal and distal sealing rings 124 and 128, 224 and 228, 324 and 328, and 424 and 428, respectively, as previously described for adaptor 20 shown in FIG. 1. Means employed to engage connector rings and sealing rings one with another forming adaptors 120, 220, 320, and 420, may be selected from techniques known to those skilled in the art of lead construction, for example insert molding resulting in mechanical interlocking and adhesive bonding.

According to embodiments of the present invention, each pair of contact zones 123, 223, 323, 423 is in an unique position for contact with a pair of connector elements selected from a plurality of connector elements, such as elements 32, 34, 36, and 38 shown in FIG. 1, when a connector, such as connector 40, is inserted into each lumen 801, 802, 803, and 804; the selected pair of connector elements corresponding with a selected pair of electrodes from a plurality of pace/sense electrodes, such as pace/sense electrodes 52, 54, 56, 58 shown in FIG. 1. When a lead, such as lead 30 illustrated in FIG. 1, is implanted, a pair of electrodes is selected, according to a position of each electrode to provide an acceptable pacing threshold and/or a quality of sensing, and/or to eliminate unwanted effects of pacing, and an appropriate adaptor from set 200 is selected for electrically coupling a selected pair of electrodes with an IMD, such as IMD 100. In one embodiment according to the present invention, each adaptor 120, 220, 320, 420 is externally labeled to indicate locations of pairs of contact zones 123, 223, 323, 423, respectively; in an alternate embodiment packaging for adaptor set 200 includes labeling to distinguish between each adaptor.

Figure 3:
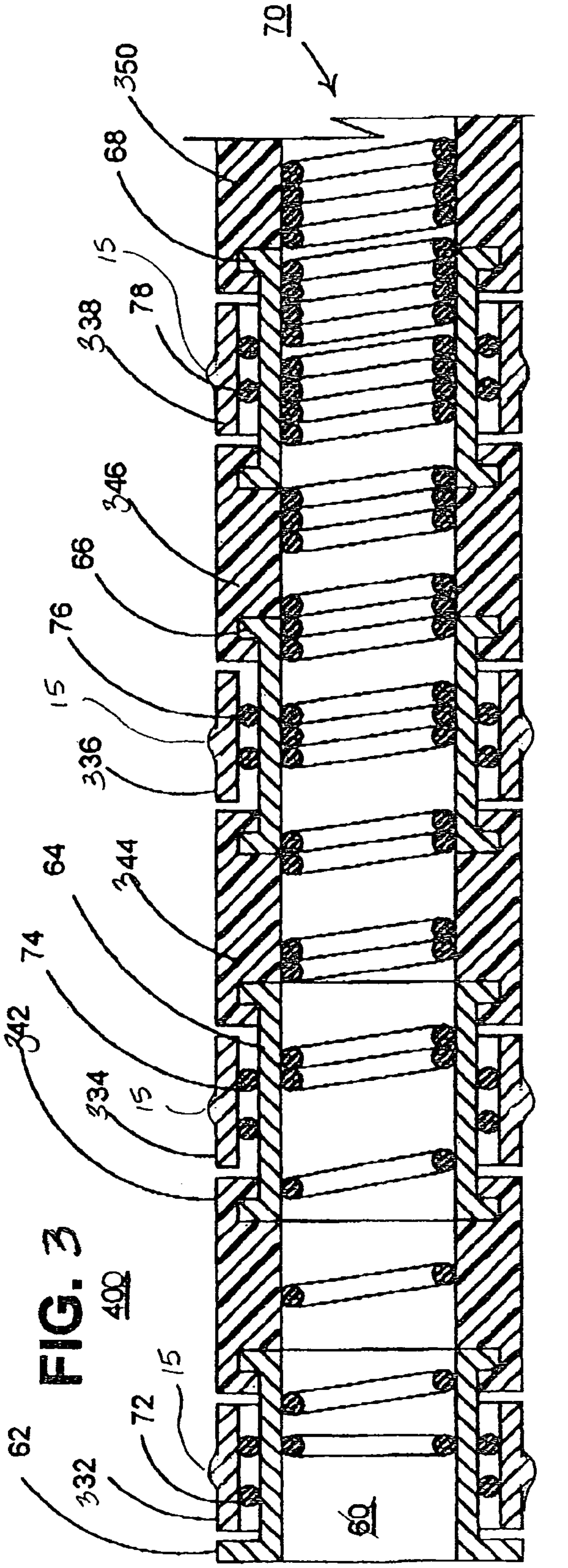
FIG. 3 is an axial cross-section of a connector according to one embodiment of the present invention.

FIG. 3 is an axial cross-section of a connector 400. It should be understood that connector 400 terminates a proximal end of a body of a lead similar to connector 40 illustrated in FIG. 1. FIG. 3 illustrates a fabrication of connector 400 according to one embodiment of the present invention, wherein a multi-filar coil 70, including electrically insulated lead conductors 72, 74, 76, and 78 wound with a common coil diameter, couples a plurality of electrodes, such as electrodes 52, 54, 56 and 58 illustrated in FIG. 1, to a plurality of connector elements 332, 334, 336, 338, respectively. As illustrated in FIG. 3, connector elements 332, 334, 336 and 338 are supported by inner crimping rings 62, 64, 66 and 68, respectively, and are electrically isolated from one another by a plurality of insulator rings 342, 344, and 346, which interlock with edges of inner crimping rings 62, 64, 66, 68. Proximal turns of the lead conductors 72, 74, 76 and 78 are stripped of insulation and extended into a space between connector elements 332, 334, 336 and 338 and respective inner crimping rings 62, 64, 66 and 68. Crimping force and/or welding is applied to make electrical and mechanical contact of the lead conductors 72, 74, 76, and 78 with the respective ring pairs 332/62, 334/64, 336/66, and 338/68. Coupling of conductors 72, 74, 76, and 78 may be achieved in a similar fashion with electrodes, such as electrodes 52, 54, 56, 58 illustrated in FIG. 1, or according to other means known to those skilled in the art of lead construction. As illustrated in FIG. 3, according to one embodiment of the present invention, connector elements 332, 334, 336, and 338 include protrusions 15 to interface with contact zones in a lumen of an adaptor, such as zones 123, 223, 323, and 423 illustrated in FIG. 2. According to one embodiment, protrusions 15 extend circumferentially; in an alternate embodiment protrusions 15 are discrete formations, of two or more positioned about a circumference of elements 332, 334, 336 and 338. FIGS. 4-7 are partial section views of connector 400 inserted within each adaptor 120, 220, 320, 420 of adaptor set 200 (FIG. 2); according to embodiments of the present invention, connector 400 is inserted into lumens 801-804 or each adaptor at a distal opening 17 until a proximal end 60 of connector 400 abuts a proximal retention ring 48 of each adaptor. FIGS. 4-7 illustrate connector 400 filted within lumens 801, 802, 803, and 804 of adaptors 120, 220, 320, and 420; according to one embodiment of the present invention, an outer diameter of lead connector 40 and a diameter of lumens 801-804 are sized to provide an interference fit, wherein contact zone pairs 123, 223, 323, and 423 are electrically coupled to selected pairs of lead connector elements 332 and 336, 334 and 336, 334 and 338, and 332 and 338, respectively, and inner surfaces of sealing rings 124, 128, 224, 228, 324, 328, 424, 428 provide electrical isolation between each of the selected pair. The interference fit may be enhanced by providing an irregular surface on the outer lead connector elements 332, 334, 336 and 338, for example by protrusions 15 illustrated in FIG. 3, or by providing resilient inward protruding surfaces of 122 and 126, 222 and 226, 322 and 326, 422 and 426 at each of contact zone pairs 123, 223, 323, 423, respectively; in a like manner, electrical isolation may be enhanced by providing resilient inward protruding surfaces on inner surfaces of sealing rings 124, 128, 224, 228, 324, 328, 424, 428.

Figure 4:
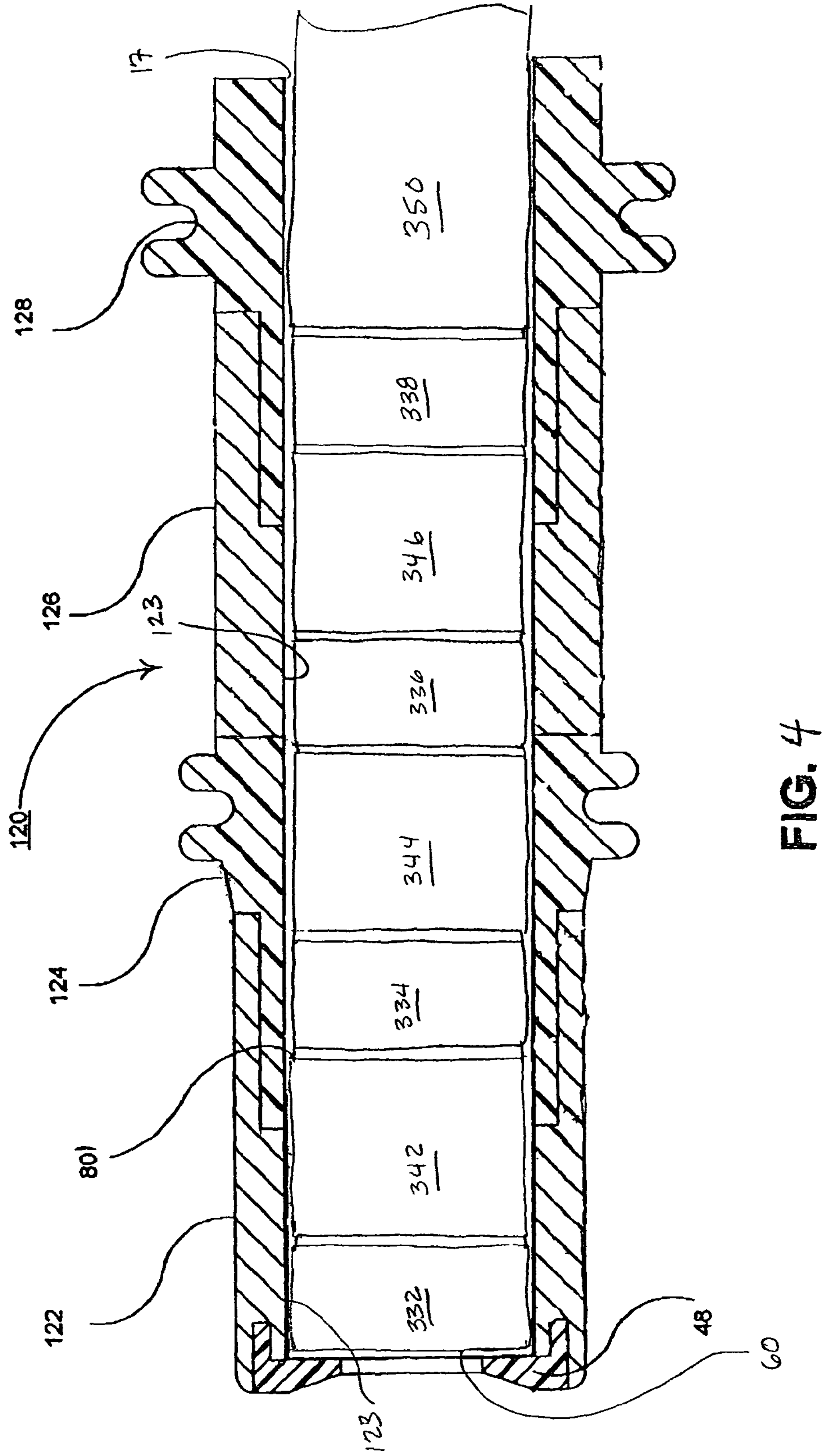
FIGS. 4-7 are partial section views of the connector shown in FIG. 3 inserted within each adaptor of the adaptor set shown in FIG. 2.
Figure 5:
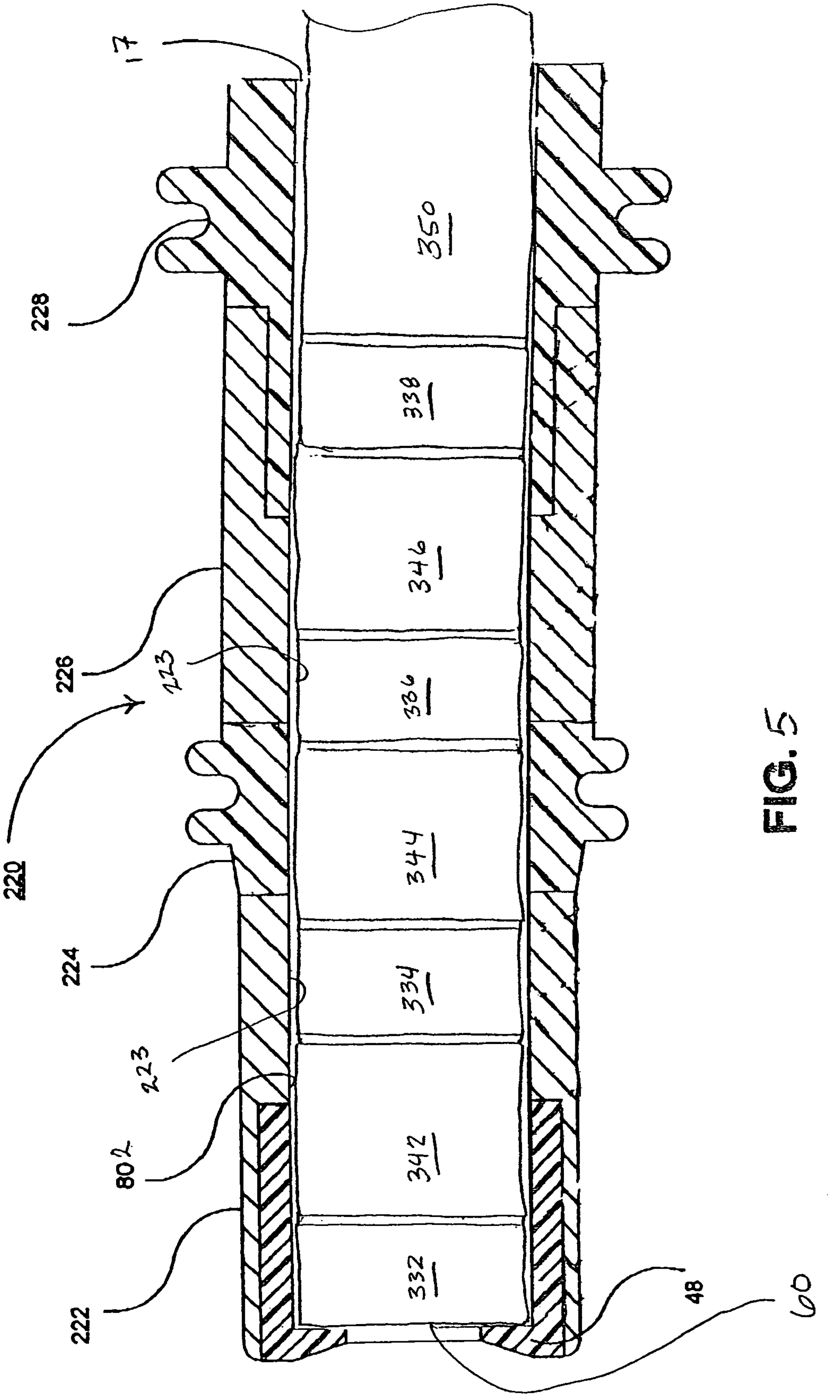
Figure 6:
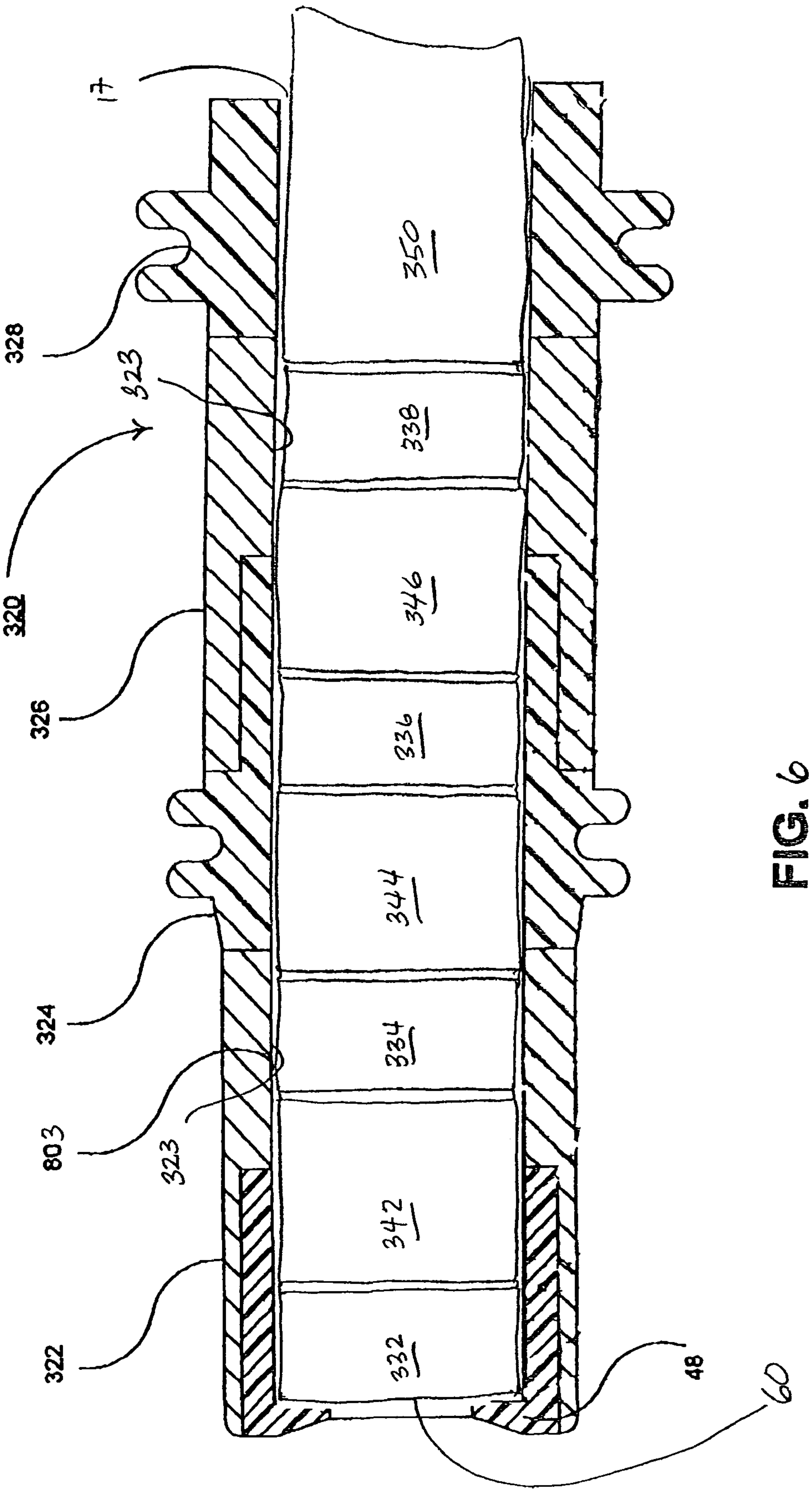
Figure 7:
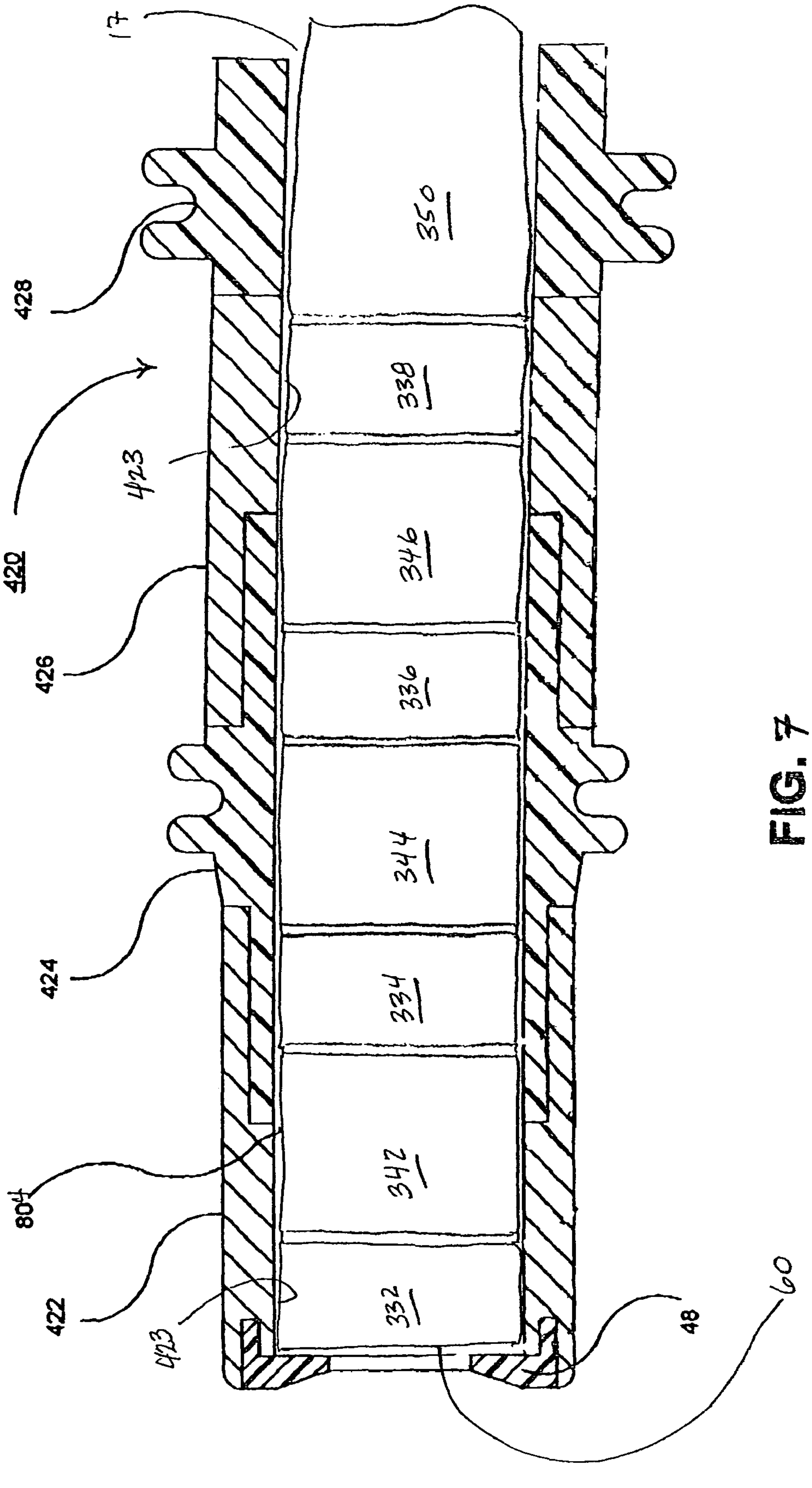

FIG. 4 illustrates adaptor 120 making electrical contact between proximal connector ring 122 and lead connector element 332 and between distal connector ring 126 and lead connector element 336 thereby facilitating coupling between selected pace/sense electrodes associated with elements 332 and 336 an the circuitry of an IMD, for example IMD 100 (FIG. 1). FIG. 5 illustrates adaptor 220 making electrical contact between proximal connector ring 222 and the connector element 334 and between distal connector ring 226 and connector element 336, facilitating selection of an alternate pair of electrodes. In a like manner, FIGS. 6 and 7 illustrate two additional selections made by fitting adaptors 320 and 420 over lead connector 400.

Figure 8:
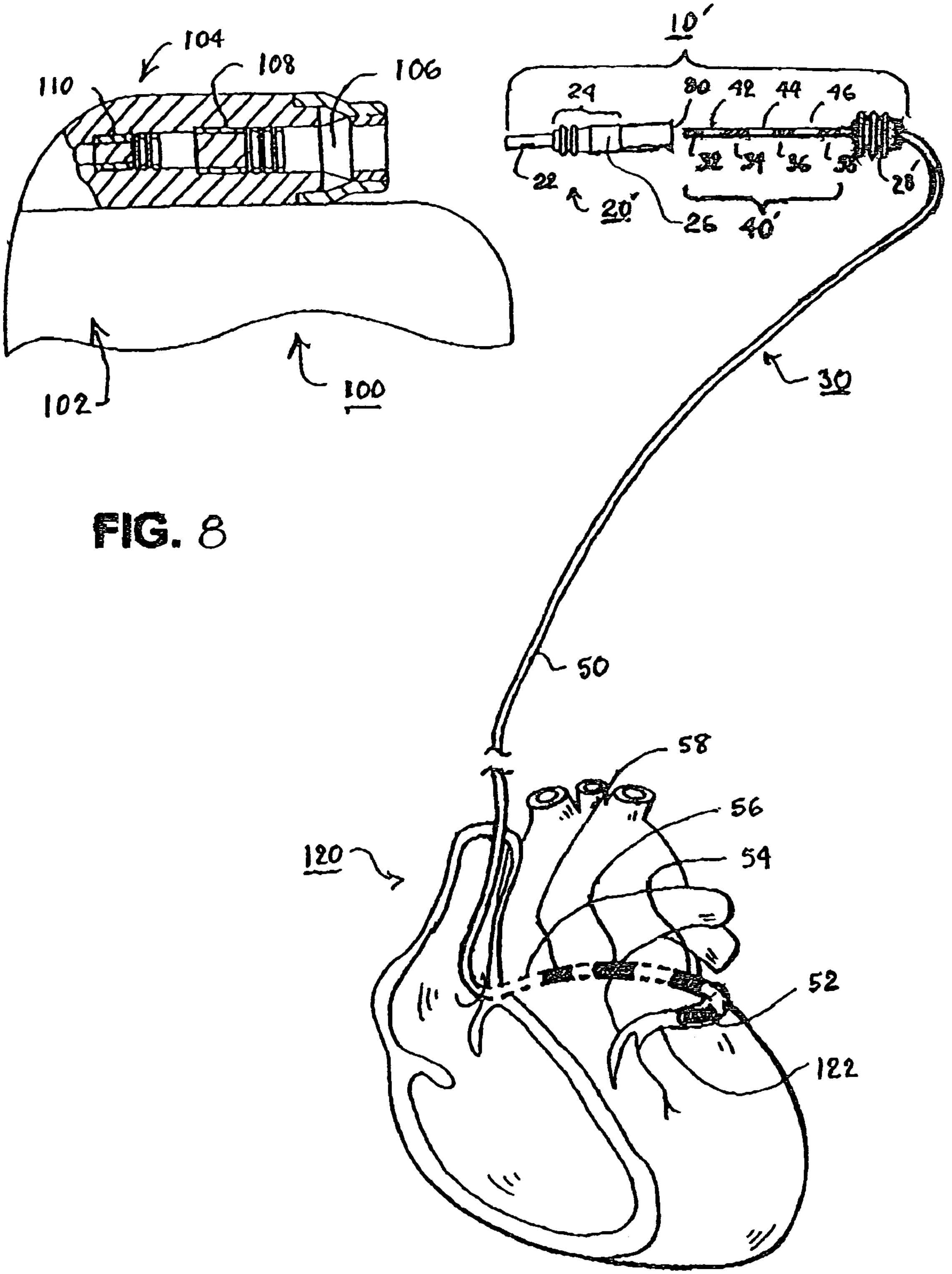
FIG. 8 is a schematic depicting an IMD in part in relation to an adaptor and a an alternate embodiment of a connector.

FIG. 8 is a schematic depicting IMD 100 in part in relation to an assembly 10' of an adaptor 20' and a connector 40' terminating a proximal end of body 50 of cardiac lead 30. FIG. 8 illustrates an alternate embodiment of the present invention wherein a distal seal set of distal sealing rings 28' is incorporated into the lead connector element array 40' rather than in the up-sizing adaptor 20'.

Figure 9:
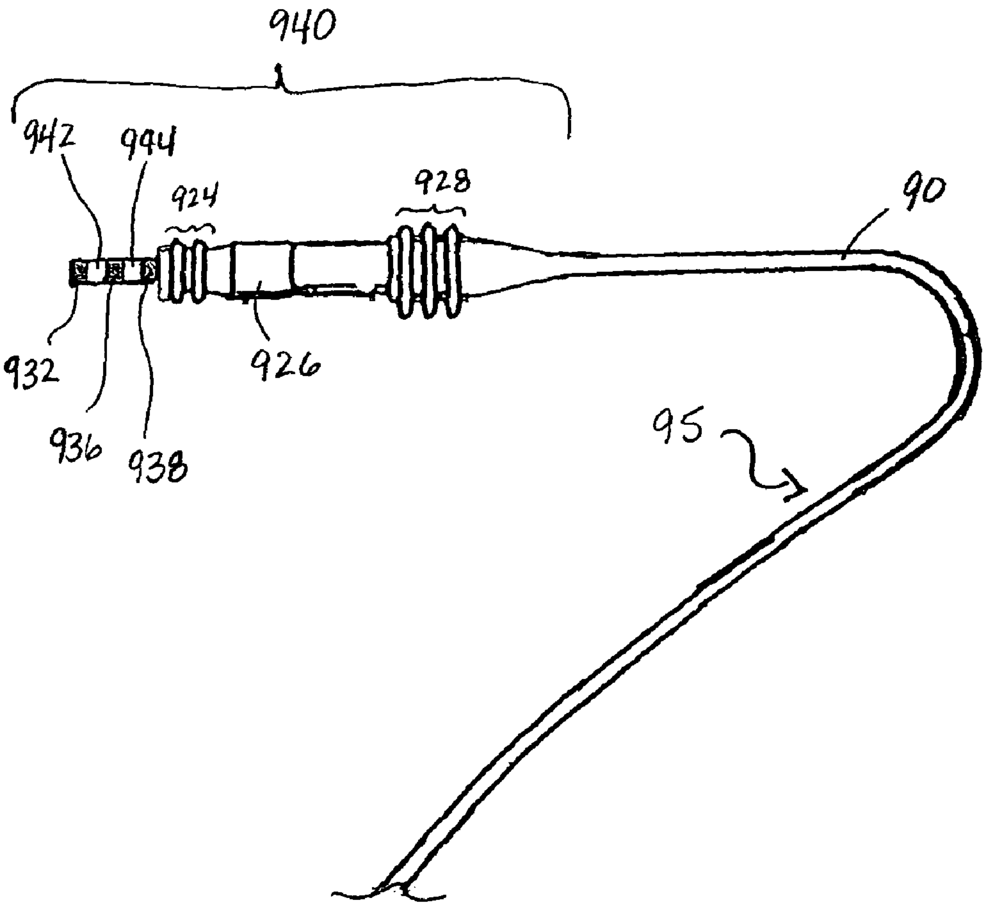
FIG. 9 is a plan view of a portion of a lead including yet another embodiment of a connector.
Figure 10:
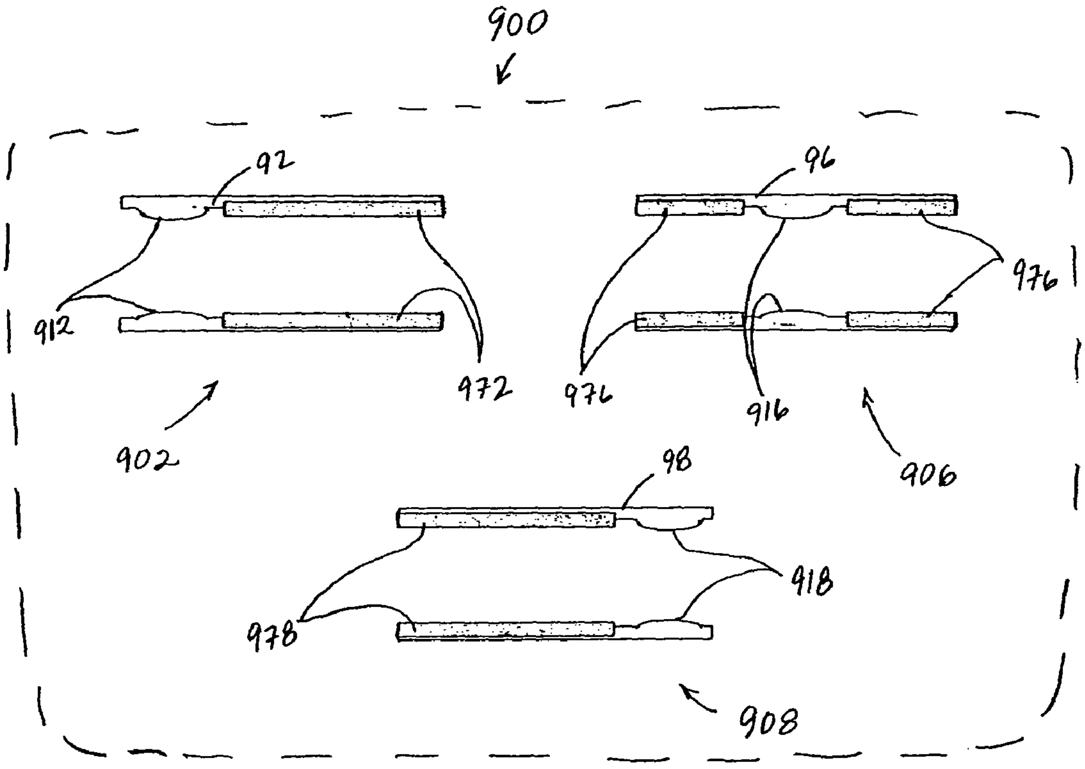
FIG. 10 is a schematic of a set of adaptors according to another embodiment of the present invention, each shown in axial cross-section and each corresponding to the lead connector shown in FIG. 9.

It will be understood that further adaptors can be devised employing variations on the combinations illustrated in FIGS. 4-8. Furthermore alternate embodiments of adaptors according to the present invention include a single contact zone positioned to electrically couple with a single connector element of a lead connector, as illustrated in FIGS. 9 and 10. FIG. 9 is a plan view of a portion of a lead 95 including a connector 940; and FIG. 10 is a schematic of a set of adaptors 900, each shown in axial cross-section, corresponding to lead connector 940 shown in FIG. 9. FIG. 9 illustrates lead 95 including a lead body 90 and connector 940 terminating a proximal end of lead body 90; connector 940 includes a connector ring 926 positioned between a distal set of sealing rings 928 and a proximal set of sealing rings 924 and is terminated by an array of connector elements 932, 936, and 938 separated by insulative zones 942 and 944. A distal portion of lead 95, not shown, includes an array of electrodes, for example electrodes 52, 54, 56, and 58 shown in FIG. 1; each electrode is electrically coupled, via conductors carried by lead body 90, to connector ring 926 and connector elements 932, 936, and 938. Coupling of array of connector elements 932, 936, 938 with respective conductors may be accomplished in a manner similar to that described for connector 400 illustrated in FIG. 3. According to embodiments of the present invention one of connector elements 932, 936, 938 corresponding to a selected electrode is electrically coupled, via an adaptor (FIG. 10), to an IMD, for example to connector block 110 within bore 106 of IMD 100 illustrated in FIG. 1, while connector ring 926 of connector 940 is directly coupled to the IMD, for example to connector block 108 of IMD 100 illustrated in FIG. 1.

FIG. 10 illustrates set of adaptors 900 including first adaptor 902, second adaptor 906 and third adaptor 908 wherein each adaptor includes a conductive shell 92, 96, 98 having an internal contact zone 912, 916, 918 and an internal insulative zone 972, 976, 978. According to embodiments of the present invention, when array of connector elements 932, 936, and 938 is inserted within first adaptor 902 only connector element 932 is electrically coupled via internal contact zone 912 to conductive shell 92; likewise when array of connector elements 932, 936, and 938 is inserted within second adaptor 906 only connector element 936 is electrically coupled to conductive shell 96 and when the array is inserted into third adaptor 908 only connector element 938 is electrically coupled to conductive shell 98. Each conductive shell 92, 96, 98 is adapted for electrical and mechanical connection with a connector block within a connector bore of an IMD, for example connector block 110 in connector bore 106 of IMD 100 described in conjunction with FIG. 1. According to some embodiments of the present invention, adaptors 902, 906, 908 are secured to connector 940 by a press fit around array of connector elements 932, 936, 938, either with or without an external securing force provided by coupling within a connector bore of an IMD.

It should be understood that, while specific embodiments have been presented in the foregoing detailed description of the invention, a vast number of variations exist. It should also be appreciated that the exemplary embodiments are only examples, and are not intended to limit the scope, applicability, or configuration of the invention in any way. For example, although unipolar and bipolar embodiments of adaptors are depicted in the figures, it will be understood that further embodiments employing sets of adaptors selecting three or more connector elements from a lead connector array fall within the scope of the present invention. In another example, although an array of connector elements has been depicted terminating a connector, adaptors according to the present invention include those configured to fit about an array of connector elements positioned anywhere along a length of a connector. Therefore, the foregoing detailed description will provide those skilled in the art with a convenient road map for implementing an exemplary embodiment of the invention. It should be understood that various changes may be made in the function and arrangement of elements described in an exemplary embodiments without departing from the scope of the invention as set forth in the appended claims.

What is claimed is:

1. A medical system comprising:

an implantable medical device including a connector bore, the connector bore comprising one or more conductive connector block portions along an inner surface;

a single lead connector including a plurality of lead connector elements electrically isolated from one another and spaced apart along the single lead connector;

a plurality of elongated insulated conductors;

a plurality of lead electrodes, each electrode of the plurality of lead electrodes coupled to a corresponding lead connector element of the plurality of lead connector elements via the plurality of elongated insulated conductors; and a set of adapters, wherein each adapter of the set of adapters is configured to be used separately from one another to electrically connect the single lead connector to the implantable medical device, wherein the set of adapters comprise:

a first adapter extending from a proximal end to a distal end, wherein the first adapter comprises:

an external surface to engage the inner surface of the connector bore, wherein the external surface comprises one or more conductive portions to electrically engage the one or more conductive connector block portions of the connector bore of the implantable medical device, an internal surface forming a lumen to receive the single lead connector, electrically isolative material defining at least a portion of the internal surface, and one or more electrical contact elements, wherein each electrical contact element of the one or more electrical contact elements is electrically coupled to a corresponding conductive portion of the one or more conductive portions of the external surface, wherein the one or more electrical contact elements are positioned along the internal surface and are electrically isolated from each other, wherein each of the one or more electrical contact elements is electrically coupled with one of the lead connector elements of the plurality of lead connector elements when the single lead connector is received within the lumen; and a second adapter extending from a proximal end to a distal end, wherein the second adapter comprises:

an external surface to engage the inner surface of the connector bore, wherein the external surface comprises one or more conductive portions to electrically engage the one or more conductive connector block portions of the connector bore of the implantable medical device, an internal surface forming a lumen to receive the single lead connector, electrically isolative material defining at least a portion of the internal surface, and one or more electrical contact elements, wherein each electrical contact element of the one or more electrical contact elements is electrically coupled to a corresponding conductive portion of the one or more conductive portions of the external surface, wherein the one or more electrical contacts are positioned along the internal surface and are electrically isolated from each other, wherein each of the one or more electrical contact elements is electrically coupled with one of the lead connector elements of the plurality of lead connector elements when the single lead connector is received within the lumen, wherein the one or more conductive portions of the external surface of the first adapter that are electrically coupled to the one or more electrical contact elements of the first adapter are located in the same location along the external surface thereof as the one or more conductive portions of the external surface of the second adapter that are electrically coupled to the one or more electrical contact elements of the second adapter, wherein at least one electrical contact element of the one or more electrical contact elements of the first adapter is located in a different location along the internal surface thereof than the one or more electrical contact elements of the second adapter, wherein at least a portion of the electrically isolative material of the first adapter is located in the same location along the internal surface thereof as at least one of the one or more electrical contact elements of the second adapter, and further wherein at least a portion of the electrically isolative material of the second adapter is located in the same location along the internal surface thereof as at least one of the one or more electrical contact elements of the first adapter.

2. The medical system of claim 1, wherein the external surface of each of the first and the second adapter conforms to an industry standard.

3. The medical system of claim 1, wherein the lead connector further includes a connector ring positioned distal to the plurality of lead connector elements for electrical connection within the connector bore.

4. The medical system of claim 3, wherein the lead connector further includes a plurality of sealing rings positioned distal to the plurality of connector elements, a first sealing ring of the plurality of sealing rings positioned proximal to the connector ring and a second sealing ring of the plurality of sealing rings positioned distal to the connector ring.

5. The medical system of claim 1, wherein each lead connector element of the plurality of lead connector elements includes an outwardly extending protrusion.

6. The medical system of claim 1, wherein the lumen of the first adapter is dimensioned to form a press fit about the plurality of lead connector elements when the plurality of lead connector elements is received within the lumen of the first adapter, and wherein the lumen of the second adapter is dimensioned to form a press fit about the plurality of lead connector elements when the plurality of lead connector elements is received within the lumen of the second adapter.

7. A method for coupling a lead connector comprising a plurality of lead connector elements to an implantable medical device including a connector bore, the connector bore comprising one or more conductive connector block portions along an inner surface, the method comprising:

selecting an adapter from a first adapter and a second adapter, wherein each adapter of the first adapter and the second adapter is configured to be used separately from one another to electrically connect the lead connector to the implantable medical device, wherein the first adapter extends from a proximal end to a distal end, wherein the first adapter comprises:

an external surface to engage the inner surface of the connector bore, wherein the external surface comprises one or more conductive portions to electrically engage the one or more conductive connector block portions of the connector bore of the implantable medical device, an internal surface forming a lumen to receive the lead connector, electrically isolative material defining at least a portion of the internal surface, and one or more electrical contact elements, wherein each electrical contact element of the one or more electrical contact elements is electrically coupled to a corresponding conductive portion of the one or more conductive portions of the external surface, wherein the one or more electrical contact elements are positioned along the internal surface and are electrically isolated from each other, wherein each of the one or more electrical contact elements is electrically coupled with one of the lead connector elements of the plurality of lead connector elements when the lead connector is received within the lumen, and wherein the second adapter extends from a proximal end to a distal end, wherein the second adapter comprises:

an external surface to engage the inner surface of the connector bore, wherein the external surface comprises one or more conductive portions to electrically engage the one or more conductive connector block portions of the connector bore of the implantable medical device, an internal surface forming a lumen to receive the lead connector, electrically isolative material defining at least a portion of the internal surface, and one or more electrical contact elements, wherein each electrical contact element of the one or more electrical contact elements is electrically coupled to a corresponding conductive portion of the one or more conductive portions of the external surface, wherein the one or more electrical contact elements are positioned along the internal surface and are electrically isolated from each other, wherein each of the one or more electrical contact elements is electrically coupled with one of the lead connector elements of the plurality of lead connector elements when the lead connector is received within the lumen, wherein the one or more conductive portions of the external surface of the first adapter that are electrically coupled to the one or more electrical contact elements of the first adapter are located in the same location along the external surface thereof as the one or more conductive portions of the external surface of the second adapter that are electrically coupled to the one or more electrical contact elements of the second adapter, wherein at least one electrical contact element of the one or more electrical contact elements of the first adapter is located in a different location along the internal surface thereof than the one or more electrical contact elements of the second adapter, wherein at least a portion of the electrically isolative material of the first adapter is located in the same location along the internal surface thereof as at least one of the one or more electrical contact elements of the second adapter, and further wherein at least a portion of the electrically isolative material of the second adapter is located in the same location along the internal surface thereof as at least one of the one or more electrical contact elements of the first adapter; and positioning the lead connector within the lumen of the selected adapter.

8. The method of claim 7, further comprising positioning the selected adapter within the connector bore of the implantable medical device.

9. A kit for coupling a lead connector having a plurality of lead connector elements within a connector bore of an implantable medical device, the connector bore comprising one or more conductive connector block portions along an inner surface, the kit comprising:

a first adapter extending from a proximal end to a distal end, wherein the first adapter comprises:

an external surface to engage the inner surface of the connector bore, wherein the external surface comprises one or more conductive portions to electrically engage the one or more conductive connector block portions of the connector bore of the implantable medical device, an internal surface forming a lumen to receive the lead connector, electrically isolative material defining at least a portion of the internal surface, and one or more electrical contact elements, wherein each of the one or more electrical contact elements is electrically coupled to a corresponding conductive portion of the one or more conductive portions of the external surface, wherein the one or more electrical contacts are positioned along the internal surface and are electrically isolated from each other, wherein each of the one or more electrical contact elements is electrically coupled with one of the lead connector elements of the plurality of lead connector elements when the lead connector is received within the lumen; and a second adapter extending from a proximal end to a distal end, wherein the second adapter comprises:

an external surface to engage the inner surface of the connector bore, wherein the external surface comprises one or more conductive portions to electrically engage the one or more conductive connector block portions of the connector bore of the implantable medical device, an internal surface forming a lumen to receive the lead connector, electrically isolative material defining at least a portion of the internal surface, and one or more electrical contact elements, wherein each electrical contact element of the one or more electrical contact elements is electrically coupled to a corresponding conductive portion of the one or more conductive portions of the external surface, wherein the one or more electrical contacts are positioned along the internal surface and are electrically isolated from each other, wherein each of the one or more electrical contact elements is electrically coupled with one of the lead connector elements of the plurality of lead connector elements when the lead connector is received within the lumen, wherein the one or more conductive portions of the external surface of the first adapter that are electrically coupled to the one or more electrical contact elements of the first adapter are located in the same location along the external surface thereof as the one or more conductive portions of the external surface of the second adapter that are electrically coupled to the one or more electrical contact elements of the second adapter, wherein at least one electrical contact element of the one or more electrical contact elements of the first adapter is located in a different location along the internal surface thereof than the one or more electrical contact elements of the second adapter, wherein at least a portion of the electrically isolative material of the first adapter is located in the same location along the internal surface thereof as at least one of the one or more electrical contact elements of the second adapter, and further at least a portion of wherein the electrically isolative material of the second adapter is located in the same location along the internal surface thereof as at least one of the one or more electrical contact elements of the first adapter, wherein each adapter of the first adapter and the second adapter is configured to be used separately from one another to electrically connect the lead connector to the implantable medical device.

10. A kit for coupling a lead connector to a medical device, wherein the medical device comprises a connector bore defining an inner surface, wherein the lead connector comprises a plurality of lead connector elements electrically isolated from one another and spaced apart along the lead connector, wherein the kit comprises a plurality of adapters, wherein the plurality of adapters comprises:

a first adapter and a second adapter, wherein each adapter of the first adapter and the second adapter is configured to be used separately from one another to electrically connect the lead connector to the medical device, wherein each of the first and the second adapters extends from a proximal end to a distal end and defines an opening configured to receive the lead connector, wherein each of the first and the second adapters further defines an external surface to engage the inner surface of the connector bore of the medical device when the adapter is received therein and an inner surface defining at least a portion of the opening to engage the lead connector when the lead connector is received therein, wherein each of the first and the second adapters comprises:

an external contact element along the external surface to electrically couple to a conductive portion on the inner surface of the connector bore of the medical device when the adapter is received therein, electrically isolative material along the internal surface, and an internal contact element along the internal surface to electrically couple to one lead connector element of the plurality of lead connector elements when the adapter receives the lead connector within the opening, wherein the internal contact element is electrically coupled to the external contact element, wherein the external contact element of the first adapter is located along the external surface of the first adapter in the same location as the external contact element of the second adapter, wherein the internal contact element of the first adapter that is electrically coupled to the external contact element of the first adapter is located along the internal surface of the first adapter in a different location than the internal contact element of the second adapter that is electrically coupled to the external contact of the second adapter, wherein at least a portion of the electrically isolative material of the first adapter is located in the same location along the internal surface thereof as the internal contact element of the second adapter, and further wherein at least a portion of the electrically isolative material of the second adapter is located in the same location along the internal surface thereof as the internal contact element of the first adapter.

11. The kit of claim 10, wherein the plurality of lead connector elements of the lead connector comprises:

a first lead connector element, and a second lead connector element, wherein the internal contact element of the first adapter is located along the internal contact surface to contact the first lead connector element when the lead connector is received within the opening of the first adapter and the internal contact element of the second adapter is located along the internal contact surface to contact the second lead connector element when the lead connector is received within the opening of the second adapter.

12. The kit of claim 11, wherein at least a portion of the electrically isolative material of the first adapter electrically isolates the second lead connector element from the internal contact element of the first adapter when the lead connector is received within the opening of the first adapter, and wherein at least a portion of the electrically isolative material of the second adapter electrically isolates the first lead connector element from the internal contact element of the second adapter when the lead connector is received within the opening of the second adapter.

13. The kit of claim 10, wherein the internal contact element of the first adapter is located along the internal contact surface a first distance away from the proximal end of the first adapter, wherein the internal contact element of the second adapter is located along the internal contact surface a second distance away from the proximal end of the second adapter, and wherein the first distance and the second distance are different.

14. The kit of claim 10, wherein the external contact element of each of the first and the second adapters comprises a ring contact.

15. The kit of claim 10, wherein the external surface of each of the first and the second adapters comprises a label, and further wherein the label of the external surface of the first adapter is different than the label of the external surface of the second adapter to distinguish between the first adapter and the second adapter.

* * * * *